(12) United States Patent
Sun et al.

(10) Patent No.: US 10,433,939 B2
(45) Date of Patent: Oct. 8, 2019

(54) MULTIPLE LAYERED DENTURE BLOCK AND/OR DISK

(71) Applicant: DENTSPLY SIRONA Inc., York, PA (US)

(72) Inventors: Benjamin Jiemin Sun, York, PA (US); Dan Ammon, York, PA (US)

(73) Assignee: DENTSPLY SIRONA Inc., York, PA (US)

( * ) Notice: Subject to any disclaimer, the term of this patent is extended or adjusted under 35 U.S.C. 154(b) by 274 days.

(21) Appl. No.: 15/641,575

(22) Filed: Jul. 5, 2017

(65) Prior Publication Data

US 2018/0055611 A1 Mar. 1, 2018

Related U.S. Application Data

(60) Provisional application No. 62/358,359, filed on Jul. 5, 2016.

(51) Int. Cl.
*A61C 13/00* (2006.01)
*A61C 13/20* (2006.01)
(Continued)

(52) U.S. Cl.
CPC ...... *A61C 13/0022* (2013.01); *A61C 13/0004* (2013.01); *A61C 13/01* (2013.01);
(Continued)

(58) Field of Classification Search
None
See application file for complete search history.

(56) References Cited

U.S. PATENT DOCUMENTS 4,115,488 A * 9/1978 Colpitts ............... A61C 13/04
264/17

5,502,087 A * 3/1996 Tateosian ............. A61C 13/20
433/168.1
(Continued)

FOREIGN PATENT DOCUMENTS

WO 0209612 A1 2/2002
WO 2013072287 A1 5/2013
(Continued)

OTHER PUBLICATIONS

International Search Report and Written Opinion of the International Searching Authority dated Oct. 30, 2017.

*Primary Examiner* — Benjamin A Schiffman
(74) *Attorney, Agent, or Firm* — Dentsply Sirona Inc.

(57) ABSTRACT

This invention designs and builds multiple layers (two layers or more) of millable dental blocks or disks for milling of various dental devices, specifically denture base blocks or disks of denture base material, where milled teeth cavities to receive artificial denture tooth materials to form final dental devices, such as partial and full dentures. This invention also designs and builds multiple layers (two layers or more) of millable denture base or denture blocks or disks comprised of denture base or/and denture tooth materials to form final dental devices, such as partial and full dentures. A method for manufacturing a layered denture is provided. The invention provides a multiple layered denture base block (or disk) for milling a denture base. The invention also provides a multiple layered denture block (or disk) for milling a denture. Highly shape adjustable or shape memory polymer layer(s) may be used in these multiple layered forms. Different layer of material has different mechanical and physical properties to meet different need, which provide added benefits to the patients, dental professional and dental laboratory.

19 Claims, 5 Drawing Sheets

(51) Int. Cl.
*A61C 13/08* (2006.01)
*B29C 39/02* (2006.01)
*A61C 13/01* (2006.01)
*A61C 13/087* (2006.01)
*A61C 13/09* (2006.01)
*B29C 39/12* (2006.01)
*B29K 33/00* (2006.01)
*B29L 31/00* (2006.01)

(52) U.S. Cl.
CPC ............ *A61C 13/04* (2013.01); *A61C 13/081* (2013.01); *A61C 13/087* (2013.01); *A61C 13/09* (2013.01); *A61C 13/20* (2013.01); *B29C 39/025* (2013.01); *B29C 39/123* (2013.01); *B29K 2033/08* (2013.01); *B29K 2033/12* (2013.01); *B29L 2031/7536* (2013.01)

(56) References Cited

U.S. PATENT DOCUMENTS

| | | | |
|---|---|---|---|
| 5,939,211 A * | 8/1999 | Mormann | A61C 13/0003 264/16 |
| 6,592,369 B2 | 7/2003 | Sun et al. | |
| 7,175,433 B2 | 2/2007 | Sun et al. | |
| 9,119,696 B2 | 9/2015 | Giordano | |
| 9,192,456 B2 | 11/2015 | Howe | |
| 9,492,252 B2 * | 11/2016 | McDermott | A61C 13/081 |
| 2008/0132603 A1 * | 6/2008 | Renz | A61K 6/083 523/115 |
| 2011/0263739 A1 * | 10/2011 | Chisholm | C08F 265/04 521/149 |
| 2015/0038634 A1 * | 2/2015 | Sun | A61K 6/083 524/504 |
| 2015/0051603 A1 * | 2/2015 | Chisholm | A61K 6/0835 606/94 |
| 2015/0245891 A1 | 9/2015 | Grobbee | |
| 2015/0245892 A1 | 9/2015 | Grobbee | |
| 2016/0243274 A1 * | 8/2016 | Chisholm | A61L 27/16 |
| 2016/0279289 A1 * | 9/2016 | Chisholm | A61L 27/16 |

FOREIGN PATENT DOCUMENTS

| | | |
|---|---|---|
| WO | 2014078537 A1 | 5/2014 |
| WO | 2015017556 A1 | 2/2015 |
| WO | 2015155447 A1 | 10/2015 |

* cited by examiner

MULTIPLE LAYERED DENTURE BLOCK AND/OR DISK

CROSS-REFERENCE TO RELATED APPLICATIONS

This patent application claims the benefit of and priority to U.S. Provisional Application Ser. No. 62/358,359, filed on Jul. 5, 2016, which is herein incorporated by reference for all purposes.

BACKGROUND

The invention provides digital dental devices using computer-aided system/computer-implemented methods. In particular, it is related to designing and manufacturing two or multiple layered blocks, disks or other forms for the fabrication of partial, full dentures or other prosthetic devices, specifically, milling partial, full dentures or other prosthetic devices and milling splints, orthodontic devices, retainers, partial or full denture bases using computer aided design and computer aided manufacturing (CAD/CAM) methods.

Dental devices, specifically for example, denture base and denture tooth should exhibit certain desirable physical characteristics to be suitable for use and offer desirable benefits to patients. They should be dimensional stable for effective functioning, sufficient strength to withstand masticating stresses and resistant to abrasion and chipping during use. They also should be durable and stable to solvents, foods, water, cold and hot and maintain esthetics without discoloration. In addition, they should be esthetics to mimic natural dentition and gum with esthetically acceptable color, i.e., close to that of natural dentition and gum. The denture base and denture tooth should not wear or deform out of occlusion, and denture base should be capable of being bonded firmly to artificial teeth. They should also be adjustable to ordinary means of physical shaping, grinding, and polishing. Denture base and denture tooth materials should be stable without discoloration and provide consistent handling properties during their shelf life. Denture fabricated from denture base and denture tooth materials should provide function, comfort and fit to the patients. It is desirable that denture base materials are compatible with hard and soft mucosal tissues. So it is desirable that denture base contains at least two different materials with different physical and mechanical properties. It is preferable that denture can be easily adjustable to provide better retention, better occlusal contact and better fit so as to provide better function, comfort and performance for patient. It is also preferable that denture can be locally adjustable while other parts remain unchanged.

Typically, denture bases are methacrylate-based acrylics, thermoplastic based or light curable resin based. Most common denture tooth materials are also methacrylate-based acrylics. In general, methacrylate-based acrylics denture bases and teeth are made out of dough from the blending of PMMA or modified PMMA polymer powders with MMA or modified MMA liquids. Denture teeth are commonly made in a tooth manufacturer. Dental lab typically uses denture teeth and denture base material from manufacturer to make denture for patient. The initial step(s) commonly used in the making a denture by making a final impression of a patient's mouth. A cast (or record base) is made of the final impression of a patient's mouth. Typically the cast is made of plaster. Then wax is shaped into the form of a denture base on the cast of the patient's mouth and artificial teeth are positioned into the denture base shaped wax. The denture base shaped wax with the artificial denture teeth is then positioned in an articulator. The artificial teeth in the denture base shaped wax are then articulated. The articulated denture base shaped wax with the artificial teeth is then positioned in a flask. The volume of the flask is filled with hardenable investment material, such as plaster. After the investment material hardens the wax is eliminated, for example by heating the flask in boiling water, leaving the artificial teeth supported by the investment material and a denture base shaped mold cavity within the investment material. After a thorough cleansing of the mold cavity a denture base material is introduced into the mold cavity. The denture base material then hardens to form a denture. The process to make a denture is long, time-consuming and labor intensive. In addition, this process produces a final denture by polymerization, where polymerization shrinkage and thermal shrinkage are introduced in the final formed denture, which adversely affect the fit of denture to the patient.

Preparation of full and partial dentures typically requires several dental office visits by each patient. The visits include labor intensive processes such as the construction of the base-plate and occlusion rims, wax try-in, invest the wax-up, wax removal and compression packing or pouring of denture base acrylic as described early. This traditional method typically resulted in a denture base containing homogeneous denture base material, which supported artificial denture teeth. A method of using light polymerizable wax like material (Eclipse system sold by Dentsply International) reduces the dental office and laboratory visits and the labor involved in making the denture, which provides a process for making a denture, comprising: articulating artificial teeth while supported by polymerizable material, whereby a denture comprising said artificial teeth is provided without forming a mold for making tooth setup volume of a denture base. The process is completed without forming wax and without applying inorganic plaster to the artificial teeth. Multiple layers of denture base materials are possible and are included in the denture base by this method. In addition, Even though lower polymerization shrinkage in Eclipse system resulted in better fitted denture, there is still polymerization shrinkage involved.

CAD/CAM systems have been using to make denture base in recent years. A disk shape homogeneous denture block is typically used for CAD/CAM milling to make denture base. These blocks are typically made of PMMA based polymer. Using acquired digital data, CAD/CAM machine mills a block to form desired denture base, where artificial denture teeth are subsequently placed into milled cavities and bonded to this denture base. Separately, some denture teeth are also milled by CAD/CAM and used to place into milled cavities and bonding to the milled denture base. This process produces the exact final denture base as designed to contact tissue side in oral cavity. Nevertheless, the fabricated denture may not fit in patient's mouth and teeth may not occlude correctly, additional adjustment or reline is needed that can be labor intensive and painful process. Denture may need to be remade that cost time, money and delay the patient care. Excessive grinding of teeth and denture base may be needed to achieve desired occlusion, which will result in the loss of esthetics of both fabricated denture base and artificial denture teeth and require additional finishing and polishing. It also faces the potential of grinding away more wear resistant enamel layers which commonly existed in some of artificial denture teeth and exposed the less wear resistant dentin layer. In order to avoid above issues, manufacturers and labs often make a try-in denture for the patient. After tried-in, adjusted and confirmed, and then duplicated the tried-in denture by milling or other fabrication methods, which adds additional steps back and requires additional office visits.

It is desirable the denture fabricated can be adjusted during final denture try-in to obtain desirable occlusion without the need of excessive of remaking, grinding, finishing and polishing. A denture fabricated where artificial denture teeth can be adjusted is highly desirable, which can avoid the need of additional tried-in step. It is also desirable the denture fabricated can be comfortable fit into oral cavity with rigid area to support artificial denture teeth and soft or relatively flexible contact surface to mucosal area for comfort and fit. Typically, denture bases are PMMA based acrylics. However, PMMA and MMA based denture bases have the disadvantage of being subject to brittle fracture due to the nature of PMMA. Rubber impact modified PMMA acrylics were used to improve their fracture toughness and impact strength. Full denture is typically formed from a rigid material since it is needed to support the artificial teeth chewing function without any movement during action. Flexible partial dentures, typically made of flexible thermoplastics, such as Nylon 12, acetal resin, etc. are being commonly used for patients, which provide comfort due to their compliance and flexibility. The use of clasps enables to stabilize the artificial denture teeth in place. The resilience and flexibility of these denture bases are limited due to the need to support artificial denture teeth. Significantly improved resiliency of tissue contact surface is desirable without compromising the artificial denture teeth stability during mastication. It is desirable to have a denture that provides a rigid ridge to support artificial denture teeth in position and resilient and flexible contact layer/area to patient's soft mucosal area for comfort and fit, which is more compatible to patient's oral cavity containing rigid ridge area and soft mucosal area. Common practice to improve the patient's comfort and fit is to reline a denture with a soft reline material, which requires additional labor intensive step. It is desirable to provide an integrated denture block or disk incorporating a soft layer or having two or more areas that offer different performances including a tooth adjustable area so as to be milled in a single step. It is desirable to provide an integrated denture block incorporating a soft liner/soft area into rigid denture base or having two or more areas that offer different performances so as to be milled in a single step. In addition, it is desirable that the contact surface of denture to mucosal area can be adjusted easily to get better fit. It is also desirable that the contact surface of denture to mucosal area can be adjusted and re-adjusted as needed, such as the need due to the ridge resorption over time. An adjustable polymer layer or a shape memory polymer is especially desirable to be used here. When digital intraoral scan is used for the fabrication of denture or denture base, a digital designed tissue side of denture may not perfectly fit to the oral cavity of the patient due to intraoral scanning involving soft tissues and an adjustable polymer layer or a shape memory polymer layer at tissue side allows the denture to be easily adjusted to the oral cavity of the patient to get the best fit and comfort. It is also desirable to have a denture, where limited tooth adjustment can be easily achieved. Denture base material around denture teeth can be easily adjusted at elevated temperature or other conditions is preferred. In addition, it is also desirable a shaded sealer/staining/paint may be used to achieve desirable esthetics/shades so that a multiple layered denture block or disk having tooth shaded layer(s) can be milled to form esthetic denture since it is highly possible that a denture milled from a multiple layered block or disk contains denture teeth having some denture base shade or denture base having some denture tooth shade. A computer or milling machine may detect shade difference or the need of sealer or painting through scanning device or code from predesigned block or disk, so as to mill extra thin layer of undesirable shaded material to accommodate the space for the application of needed shaded sealer.

Even though this invention referred mainly to denture, denture base and teeth, the disk or block of this invention is not limited to the milling of denture, denture teeth or denture base, they can be made into various shapes and shades and can be used to mill various dental devices, such as splints, nightguards, flexible partial dentures, flippers, orthodontic devices, aligners, retainers, frames, surgical guides, dental appliances, etc. The different layers of dental materials offer the dental devices with different performances, similar to denture and denture base with varied adjustability, physical properties and shape memory performance. Their shades can be formed from clear to highly pigmented shade. For example, a clear disk or block with multiple layers can be used to mill a multiple layered nightguard, where the hard and wear resistant top surface layer can effectively withstand wearing and grinding while a flexible or resilient side or the area below surface contact in nightguard can provide comfort, retention, adjustability and easy insertion and easy removal for the patient. Moreover, a surface adjustable layer can offer easy occlusion at chairside or in dental laboratory without the need to grind away materials to achieve desired occlusion. The denture base or denture tooth materials mentioned in this invention can be easily referred as dental materials, such as nightguard materials, retainer materials, or aligner materials, etc.

Grobbee (US patent application publication No. US20150245891 and US20150245892) claimed a method of manufacturing a layered denture in which the enamel layer is manufactured first from an enamel material blank, a dentin layer is formed and machined from the first denture material, and the denture base is manufactured last from the second denture material.

Giordano (U.S. Pat. No. 9,119,696) disclosed a dental blank has at least an inner zone of a first color and an outer zone of a second color, wherein the inner and outer zones are concentric. The dental blank has a geometric shape, wherein the inner zone is surrounded in its entirety by the outer zone such that only the outer zone is visible on all surfaces of the blank and the inner zone is not visible on any surface of the blank.

Howe (U.S. Pat. No. 6,641,938) claimed a method of milling a block of denture base material to form the first cavity to receive first denture tooth material and cured, milling the first denture tooth material to form the plurality of teeth. Final milling to form final denture comprised of a denture base and denture teeth.

SUMMARY OF THE INVENTION

In one aspect, the present invention is directed to a method for making a multilayered block or disk comprising the steps of: providing a mold; placing a first polymerizable material in the mold to form a first layer, the first polymerizable material including a mixture of: a powder blend of 65% to 85% by wt a [methyl (meth)acrylate, ethyl (meth)acrylate and butyl (meth)acrylate] copolymer; and a first initiator; and a liquid blend of 4-15% by wt a first rubber impact modifier; at least one monomer; and a second initiator; placing a second polymerizable material in contact with the first layer of the polymerizable material to form a second polymerizable layer, wherein the second polymerizable material is different than the first polymerizable material and includes a mixture of: a powder blend having of 75% to about 95% by wt [methyl (meth)acrylate, ethyl (meth)acrylate and butyl (meth)acrylate] copolymer; and a third initiator; a liquid blend of 4-12% by wt a second rubber impact modifier being different than the first rubber impact modifier; 1-10% by wt of at least one dimethacrylate component; and 20-70% by wt at least one methacrylate based component, and a fourth initiator; curing the first polymerizable material to formed a cured first polymerizable material; curing the second polymerizable material to form a second polymerizable material, the cured first polymerizable material and the cured second polymerizable material form the multilayered block or disk; wherein the cured second polymerizable material has a higher Tg than the cured first polymerizable material.

In another aspect of the present invention, it is contemplated to provide a multiple layered dental block (or disk) for CAD/CAM milling a dental device.

In another aspect of the present invention, it is contemplated to provide a process for making a multiple layered dental block (or disk).

In another aspect of the present invention, it is contemplated to provide a multiple layered denture base or denture block (or disk) for CAD/CAM milling a denture base or denture.

In another aspect of the present invention, it is contemplated to provide a process for making a multiple layered denture block (or disk), comprising: placing first layer of polymerizable denture base material at a specific location and curing, adding additional layers of polymerizable denture base and denture tooth materials (at least one layer) with specific forms and at specific locations and curing them layer by layer.

In another aspect of the present invention, it is contemplated to provide a process for making a multiple layered denture block (or disk), comprising: placing first layer and second layer of polymerizable denture base materials, adding additional layers of polymerizable denture tooth materials (at least one layer) and then curing them together.

In another aspect of the present invention, it is contemplated to provide a process for making a multiple layered denture base block (or disk), comprising: placing first layer and second layer of polymerizable denture base materials, adding additional layers of polymerizable denture base materials as needed and then curing them together.

In another aspect of the present invention, it is contemplated to provide a shaded sealer to locally apply on denture so as to obtain desired shades and esthetics.

In another aspect of the present invention, it is contemplated to provide a process for making a multiple layered denture block (or disk), comprising: placing first layer of polymerizable denture base materials at specific areas, adding additional layers of polymerizable denture tooth materials (at least one layer) as needed at specific areas and then curing them together.

In another aspect of the present invention, it is contemplated to provide a process for making a multiple layered denture block (or disk), comprising: placing first layer and second layer of polymerizable denture base materials at specific areas, adding additional layers of polymerizable denture tooth materials (at least one layer) as needed at specific areas and then curing them together.

In another aspect of the present invention, it is contemplated to provide a process for making a multiple layered denture base block (or disk), comprising: placing first layer and second layer of polymerizable denture base materials at specific areas separately, adding additional layers of polymerizable denture base materials as needed at specific areas and then curing them together.

In another aspect of the present invention, it is contemplated to provide a process for making a multiple layered denture base or denture block (or disk), comprising: placing first layer of polymerizable material and curing first layer of polymerizable material to form first cured layer, then placing second layer material and then curing to form second cured layer. Additional layers of denture base/tooth materials may be added and cured as needed.

In another aspect of the present invention, it is contemplated to provide a process for making a multiple layered denture base or denture block (or disk), comprising: placing first layer of polymerizable material at specific location and curing first layer of polymerizable material, then placing second layer material at another specific location and then curing to form second cured layer. Additional layers of denture base/tooth materials may be added to specific locations and cured as needed.

In another aspect of the present invention, it is contemplated to provide a process for making a multiple layered denture block (or disk), comprising: placing first layer of polymerizable material and curing first layer of polymerizable material, then placing second layer material and then curing to form second cured layer. Additional layers of polymerizable denture base materials may be added and cured as needed. Then the layers of denture tooth materials may be added and cured layer by layer on cured denture base materials to form a block (or disk) containing both one or more layers of denture base area and one or more layers of denture tooth area.

In another aspect of the present invention, it is contemplated to provide a process for making a multiple layered denture block (or disk), comprising: placing first layer of polymerizable material at specific location and curing first layer of polymerizable material, then placing second layer material at another specific location and then curing to form second cured layer. Additional layers of polymerizable denture base materials may be added to specific locations and cured as needed. Then the layers of denture tooth materials may be added to specific locations and cured layer by layer on cured denture base materials to form a block (or disk) containing both one or more layers of denture base area and one or more layers of denture tooth area.

In another aspect of the present invention, it is contemplated to provide a process for making a multiple layered denture block (or disk), comprising: placing first layer and second layer of polymerizable denture base materials, adding additional layers of polymerizable denture base materials as needed and then curing them together. Then the layers of denture tooth materials may be added and cured layer by layer or together on cured denture base materials to form a block (or disk) containing both one or more layers of denture base area and one or more layers of denture tooth area.

In another aspect of the present invention, it is contemplated to provide a process for making a multiple layered denture block (or disk), comprising: placing first layer and second layer of polymerizable denture base materials at specific areas separately, adding additional layers of polymerizable denture base materials as needed at specific areas and then curing them together. Then the layers of denture tooth materials may be added and cured layer by layer or together on cured denture base materials to form a block (or disk) containing both one or more layers of denture base area and one or more layers of denture tooth area.

In another aspect of the present invention, it is contemplated to provide a process for making a multiple layered denture block (or disk), comprising: placing first layer and second layer of polymerizable denture base materials, adding additional layers of polymerizable denture base materials as needed. Then the layers of denture tooth materials may be added and cured together or layer by layer to form a block (or disk) containing both one or more layers of denture base area and one or more layers of denture tooth area.

In another aspect of the present invention, it is contemplated to provide a process for making a multiple layered denture block (or disk), comprising: placing first layer and second layer of polymerizable denture base materials at specific areas separately, adding additional layers of polymerizable denture base materials as needed at specific areas and then curing them together. Then the layers of denture tooth materials may be added and cured together or layer by layer to form a block (or disk) containing both one or more layers of denture base area and one or more layers of denture tooth area.

In another aspect of the present invention, it is contemplated to provide a block (or disk) having different shades and hues at different layers and different spots.

In another aspect of the present invention, it is contemplated to provide a multiple layered block (or disk) having different shades and hues at different layers and different spots.

In another aspect of the present invention, it is contemplated to provide a block (or disk) having different layer materials with different mechanical and physical properties.

In another aspect of the present invention, it is contemplated to provide a block (or disk) containing different layer materials ranged from resilient materials with low Tg, to flexible materials and rigid materials with high Tg.

In another aspect of the present invention, it is contemplated to make a multiple layered denture base, where the different layers of materials can be uncured, partially cured or fully cured.

In another aspect of the present invention, it is contemplated to make a multiple layered denture base, where the different layers of materials have different mechanical and physical properties.

In another aspect of the present invention, it is contemplated to provide a multiple layered denture base block (or disk), where the denture base materials around denture teeth area of milled denture from this block can be adjusted while the rest of denture and tissue side remain shape stable at elevated temperature up to 100 C.

In another aspect of the present invention, it is contemplated to provide a multiple layered denture base block (or disk), where the denture base materials around denture teeth area of milled denture from this block is shape stable while the rest of denture and tissue side are adjustable at elevated temperature up to 100 C.

In another aspect of the present invention, it is contemplated to provide a multiple layered denture base block (or disk), where the denture base materials around denture teeth area and tissue side area of milled denture from this block can be adjustable while the rest of denture is shape stable at elevated temperature up to 100 C.

In another aspect of the present invention, it is contemplated to make a multiple layered dental device, where the different layers of materials can be uncured, partially cured or fully cured.

In another aspect of the present invention, it is contemplated to make a multiple layered dental device, where the different layers of materials have different mechanical and physical properties.

In another aspect of the present invention, it is contemplated to provide a multiple layered dental device, where the top contact surface is highly wear resistance and shape stable while the side or area below surface layer is highly adjustable at adjustable condition.

In another aspect of the present invention, it is contemplated to provide a multiple layered dental device, where the top contact surface is highly adjustable while the side or area below surface layer is shape stable at adjustable condition.

In yet another aspect of the present invention, it is contemplated that the high strength dental composition has one or any combination of the following features: wherein the cured first polymerizable material has flexural strength ranging from 70 to 110 MPa (85 to 100 MPa); wherein the cured first polymerizable material has a flexural modulus ranging from 2000 to 3500 MPa (2400 to 3200 MPa); wherein the cured second polymerizable material has flexural strength ranging from 115 MPa to 200 MPa (125 to 175 MPa); wherein the cured second polymerizable material has a flexural modulus ranging from 2400 MPa to 3700 MPa (3000 to 3500 MPa); wherein the first polymerizable material is cured prior to the curing of the second polymerizable material; wherein the step of placing the second polymerizable material occurs after the step of curing the first polymerizable material; wherein the first layer of polymerizable material, after being cured includes recesses for receiving the second polymerizable material; wherein the cured first layer of polymerizable material forms a denture base and the cured second layer of polymerizable material forms a plurality of teeth after a further step of milling or grinding the multilayered block or disk; wherein the second polymerizable material extends above the recesses while forming the second layer of polymerizable material; wherein the step of curing the first polymerizable material and the step of curing the second polymerizable material occur at the same time; wherein the step of placing the second polymerizable material occurs after the step of curing the first layer of polymerizable material; further comprising the step of placing a third polymerizable material in contact with the second layer of polymerizable material to form a third layer of polymerizable material; wherein the step of placing the third polymerizable material occurs after the step of curing the second layer of polymerizable material; further comprising the step of curing the third layer of polymerizable material; wherein the cured first layer of polymerizable material around recesses formed therein having the cured second polymerizable material, after being milled or grinded is adjustable while the remaining areas of the cured first polymerizable material and the cured second polymerizable material remain shape stable at elevated temperatures up to 100° C.; wherein the curing steps, the first polymerizable material and the second polymerizable material are partially cured to form a partially cured multilayered disk or block; further comprising the steps of: milling or grinding the partially cured multilayered block or disk to form a partially cured dental component; and curing the milled or ground partially cured block or disk to form a fully cured dental component; wherein the fully cured dental component is a denture having a denture base formed for the milled or ground fully cured first polymerizable material and a plurality of teeth formed from the milled or ground fully cured second polymerizable material; wherein the top surface of the teeth formed from the milled or ground fully cured second polymerizable material has a high wear resistance determined by volume loss ranging from 0.045-0.120 mm$^3$ at 37° C. (after 400,000 cycles at 50 RPM); or any combination thereof.

DETAILED DESCRIPTION OF THE INVENTION

Figure 1A:
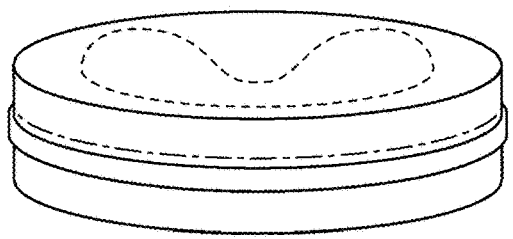
FIG. 1A is seen a schematic view of a disk with two layered denture base materials.
Figure 1B:
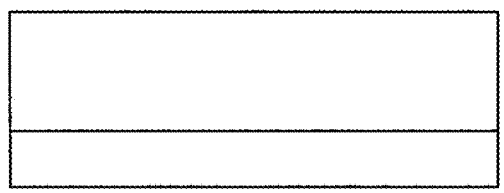
FIG. 1B is a schematic side cross-sectional view of a disk of cured denture base materials comprising of two layers.
Figure 1C:
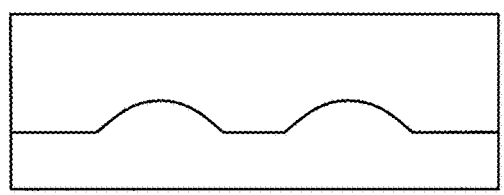
FIG. 1C is another schematic side cross-sectional view of a disk of cured denture base materials comprising of two layers.
Figure 1D:
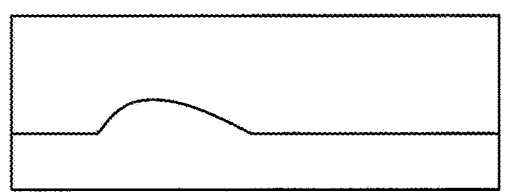
FIG. 1D is yet another schematic side cross-sectional view of a disk of cured denture base materials comprising of two layers.
Figure 2A:
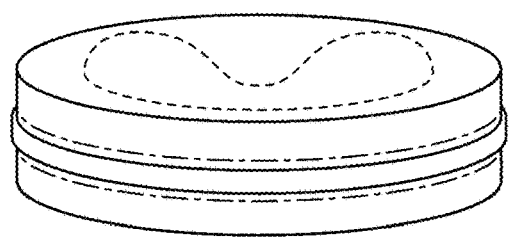
FIG. 2A is seen a schematic view of a multiple layered disk containing three cured denture base and cured denture tooth material layers.
Figure 2B:
FIG. 2B is seen a schematic side cross-sectional view of a disk containing three cured denture base and cured denture tooth layers.
Figure 2C:
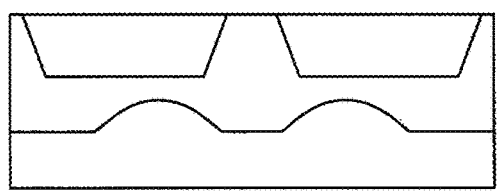
FIG. 2C is another schematic side cross-sectional view of a disk containing three cured denture base and cured denture tooth layers.
Figure 2D:
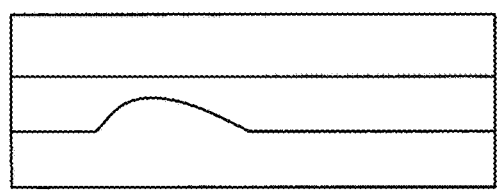
FIG. 2D is yet another schematic side cross-sectional view of a disk containing three cured denture base and cured denture tooth layers.
Figure 2E:
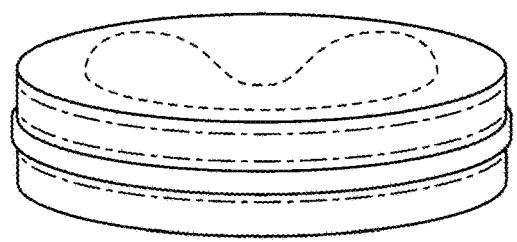
FIG. 2E is seen a schematic view of a multiple layered disk containing four cured denture base and cured denture tooth material layers.
Figure 2F:
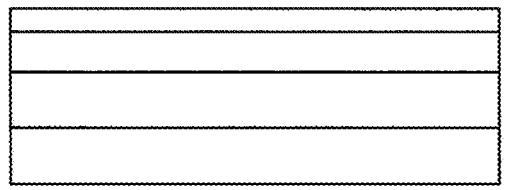
FIG. 2F is a schematic side cross-sectional view of a disk containing four cured denture base and cured denture tooth layer.
Figure 2G:
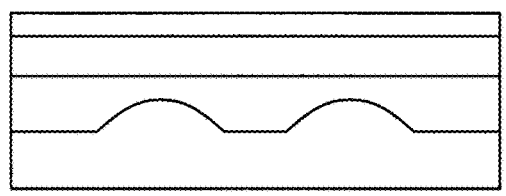
FIG. 2G is another schematic side cross-sectional view of a disk containing four cured denture base and cured denture tooth layers.
Figure 2H:
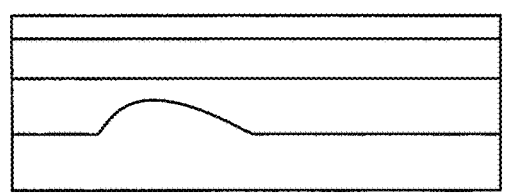
FIG. 2H is yet another schematic side cross-sectional view of a disk containing four cured denture base and cured denture tooth layers.
Figure 2I:
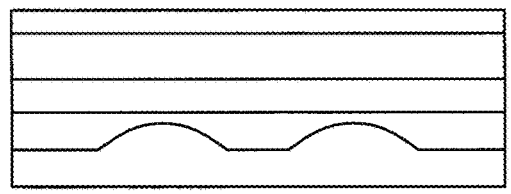
FIG. 2I is a schematic side cross-sectional view of a disk containing cured five layers of denture base and denture tooth.
Figure 2J:
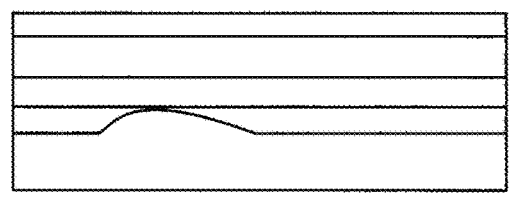
FIG. 2J is another schematic side cross-sectional view of a disk containing cured five layers of denture base and denture tooth.
Figure 2K:
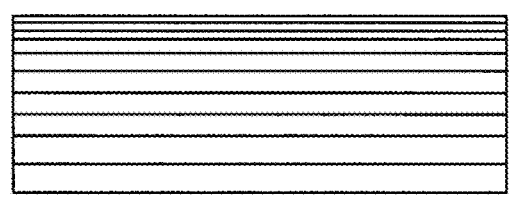
FIG. 2K is a schematic side cross-sectional view of a disk containing cured many layers of denture base and many layers of denture tooth.
Figure 2L:
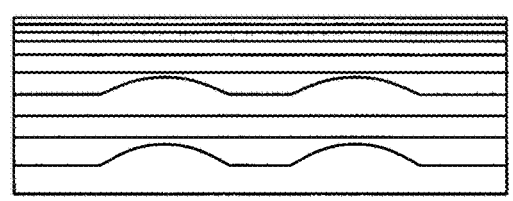
FIG. 2L is another schematic side cross-sectional view of a disk containing cured many layers of denture base and many layers of denture tooth.
Figure 3:
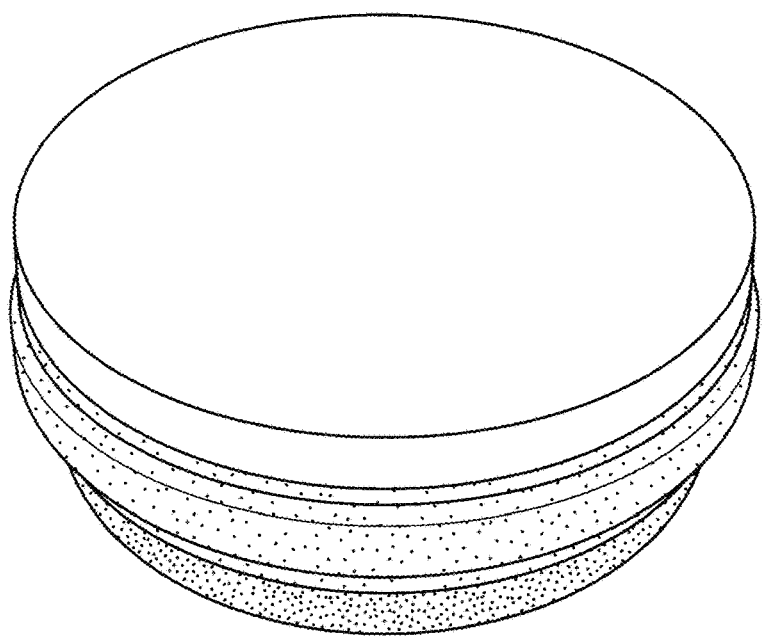
FIG. 3 is a perspective view of a cured multilayered (three-layered) disk having a first colored top layer, a second colored middle layer, and a third colored bottom layer, the flexural strength of the top layer being higher than the flexural strength of the middle layer and the flexural strength of the middle layer being higher than the flexural strength of the bottom layer.
Figure 4:
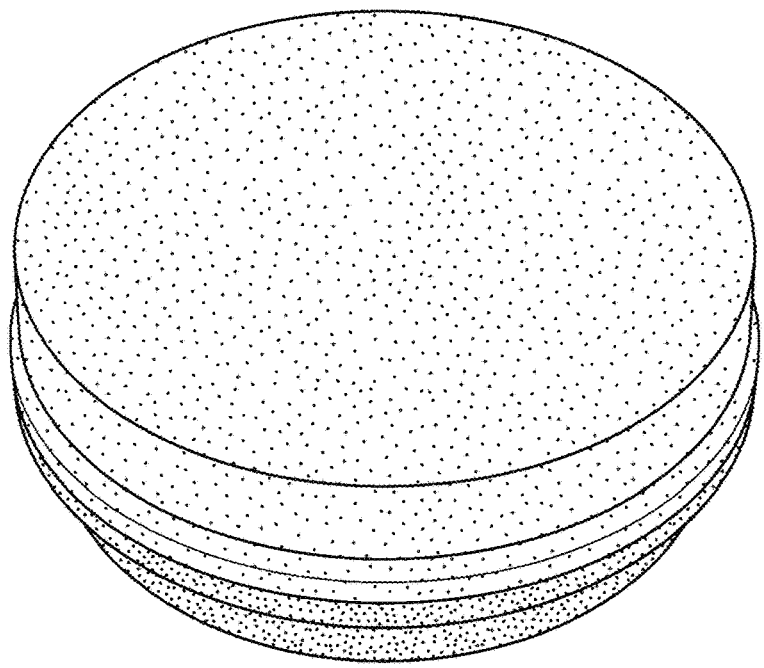
FIG. 4 is a perspective view of another cured multilayered (dual-layered) disk having a first colored top layer and a second colored bottom layer, the flexural strength of the top layer being higher than that of the bottom layer.

The invention is now described with more particular reference to FIGS. 1A through 2L. With particular reference to FIG. 1A is seen a schematic view of a disk of cured two layered denture base materials. Two layers of denture base materials may not level each other at contact area, which may form arch form, egg form, or cup form, etc. to mimic various possible denture forms for each layer. FIG. 1B is a schematic side cross-sectional view of a disk of cured denture base materials comprising of two layers. FIG. 1C is another schematic side cross-sectional view of a disk of cured denture base materials comprising of two layers. FIG. 1D is yet another schematic side cross-sectional view of a disk of cured denture base materials comprising of two layers as shown in FIG. 1A to 1C. FIG. 2A is seen a schematic view of a three layered disk containing two layer cured denture base materials and one cured denture tooth material layer or three layers of cured denture base materials. FIG. 2B is seen a schematic side cross-sectional view of a disk containing one cured denture base and two cured denture tooth layers, two cured denture base and one cured denture tooth layers or three layers of cured denture base materials. FIG. 2C is another schematic side cross-sectional view of a disk containing one cured denture base and two cured denture tooth layers, two cured denture base and one cured denture tooth layers or three layers of cured denture base materials. FIG. 2D is yet another schematic side cross-sectional view of a disk containing one cured denture base and two cured denture tooth layers, two cured denture base and one cured denture tooth layers or three layers of cured denture base materials. These layers may appear as arch form, egg form, or cup form, etc. in disk, block or any shape for various possible denture configurations for each layer. FIG. 2E is seen a schematic view of a multiple layered disk containing four layers of the various combinations of denture base and denture tooth materials. FIG. 2F is a schematic side cross-sectional view of a disk containing four layers of the various combinations of denture base and denture tooth materials. FIGS. 2G and 2H are additional schematic side cross-sectional views of a disk containing four layers of the various combinations of denture base and denture tooth materials. FIG. 2I is a schematic side cross-sectional view of a disk containing five layers of the various combinations of denture base and denture tooth materials. FIG. 2J is another schematic side cross-sectional view of a disk containing five layers of the various combinations of denture base and denture tooth materials. FIG. 2K is a schematic side cross-sectional view of a disk containing multiple layers of denture base and denture tooth materials. FIG. 2L is another schematic side cross-sectional view of a disk containing multiple layers of denture base and denture tooth materials. These layers in disks or blocks can be formed by solidification upon cooling, polymerization by light irradiation, self-cure or heat cure after mixing from two parts materials. They can be made by injecting, molding, pouring, packing, flowing, compressing, jetting, printing, and layering, etc.

This invention is mainly related to a millable block, disk, or other forms for making removal dental prostheses, such as partial and full dentures, splints, retainers, aligners, etc. Denture block can be fully cured, uncured or partially cured prior to milling. A part of denture block can be fully or partially cured and a part of denture block can be partially cured or uncured. Partially cured blocks (disks) can be fully cured by light, heat, the combination of light and heat and then final milled to form final dental devices, such as dentures, partial dentures, nightguard, etc. Partially or uncured part may be milled prior to the final cure. Partial cured or uncured blocks (disks) can be milled much faster and easier, with less wear of milling tools, such as burs.

One of the features of the millable block of this invention is that it contains at least two layers of different materials in this block. The different materials may form in several specific arch forms as shown in Figures to accommodate different denture forms for the patients. The layers may be substantially parallel to the surface of block, or they may be substantially arch shaped, full or half elliptical shaped, half-bell shaped, full or half circle shaped, or full or half cup shaped, etc. to the surface of block, Additional feature includes at least two layers of different or same materials in this block may have at least two different shades.

It is also preferable that the highly wear resistant tooth material layers formed a u-shape or arch shape in this puck (disk, etc.) so as to minimize the need to mill those high wear resistant tooth materials.

In a preferred embodiment of the invention, a layer of polymerizable denture base material was placed (molded, added, poured, jetted, flowed, injected or sprayed, etc.) to form a first layer of denture block form, which is uncured, partially cured or fully cured to form first layer of denture base at desired location. Subsequently, a second layer of polymerizable denture base material was placed (molded, added, poured, jetted, flowed, injected or sprayed, etc.) on top of first layer denture base to form a second denture base layer of denture block form, which is uncured, partially cured or fully cured to form second layer of denture base at desired location. Additional layers might be applied as needed. Alternatively, additional final cure may be applied for this block.

In another preferred embodiment of the invention, a layer of polymerizable denture base material was placed (molded, added, poured, jetted, flowed, injected or sprayed, etc.) to form a first layer of denture block form, which is uncured, partially cured or fully cured to form first layer of denture base at desired location. Subsequently, a first layer of polymerizable denture tooth material was placed (molded, added, poured, jetted, flowed, injected or sprayed, etc.) on top of first layer denture base to form a first denture tooth layer of denture block form, which is uncured, partially cured or fully cured to form second layer of denture base at desired location. Then another layer of polymerizable denture tooth material was placed (molded, added, poured, jetted, flowed, injected or sprayed, etc.) on top of first denture tooth layer to form a second denture tooth layer of denture block form, which is uncured, partially cured or fully cured to form second denture tooth layer of denture block at desired location. Alternatively, additional final cure may be applied for this block.

In yet another preferred embodiment of the invention, a layer of polymerizable denture base material was placed (molded, added, poured, jetted, flowed, injected or sprayed, etc.) to form a first layer of denture block form, which is uncured, partially cured or fully cured to form first layer of denture base at desired location. Subsequently, a second layer of polymerizable denture base material was placed (molded, added, poured, jetted, flowed, injected or sprayed, etc.) on top of first layer denture base to form a second denture base layer of denture block form, which is uncured, partially cured or fully cured to form second layer of denture base at desired location. Additional layers of denture base materials might be applied as needed. Then, a first layer of polymerizable denture tooth material was placed (molded, added, poured, jetted, flowed, injected or sprayed, etc.) on top of denture base layers to form a first denture tooth layer of denture block form, which is uncured, partially cured or fully cured to form first layer of denture tooth material at desired location. Another layer of polymerizable denture tooth material was placed (molded, added, poured, jetted, flowed, injected or sprayed, etc.) on top of first denture tooth layer to form a second denture tooth layer of denture block form, which is uncured, partially cured or fully cured to form second denture tooth layer of denture block at desired location. Additional layers of denture tooth materials might be applied as needed. Alternatively, additional final cure may be applied for this block.

In yet another preferred embodiment of the invention, a layer of shape memory polymeric material was placed (molded, added, or injected, etc.) to form a first layer of denture block form. Subsequently, a second layer of polymerizable denture base material was placed (molded, added, poured, jetted, flowed, injected or sprayed, etc.) on top of first layer denture base to form a second denture base layer of denture block form, which is uncured, partially cured or fully cured to form second layer of denture base at desired location. Additional layers of various denture base materials might be applied as needed. Alternatively, additional final cure may be applied for this block.

In yet another preferred embodiment of the invention, a layer of shape memory polymeric material was placed (molded, added, or injected, etc.) to form a first layer of denture block form. Subsequently, a second layer of polymerizable denture base material was placed (molded, added, poured, jetted, flowed, injected or sprayed, etc.) on top of first layer denture base to form a second denture base layer of denture block form, which is uncured, partially cured or fully cured to form second layer of denture base at desired location. Additional layer of polymerizable denture base material was placed (molded, added, or injected, etc.) to form a shape memory polymer layer in denture block form before the tooth layers. Then, a first layer of polymerizable denture tooth material was placed (molded, added, poured, jetted, flowed, injected or sprayed, etc.) on top of denture base layers to form a first denture tooth layer of denture block form, which is uncured, partially cured or fully cured to form first layer of denture tooth material at desired location. Another layer of polymerizable denture tooth material was placed (molded, added, poured, jetted, flowed, injected or sprayed, etc.) on top of first denture tooth layer to form a second denture tooth layer of denture block form, which is uncured, partially cured or fully cured to form second denture tooth layer of denture block at desired location. Additional layers of denture tooth materials might be applied as needed. Alternatively, additional final cure may be applied for this block. Both the contour of tissue side and the positions of denture teeth of denture milled from this block can be adjusted repeatedly and independently once heated to a specific temperature since the shape memory polymeric materials at tissue side and around denture teeth have different phase transition temperatures or different phase transition mechanisms.

For some types of artificial tooth or denture base materials, bonding agents may be preferably applied between selected layers to achieve integral connected denture teeth and denture base as well as between different layers in denture teeth. Specially, a thin layer of bonding liquid may be sprayed on the milled denture base prior to the application of dentin material, or a thin layer of bonding liquid may be applied on milled dentin part of tooth prior to apply next shaded dentin or enamel material.

The invention provides multiple layered blocks, having an integral denture base layers with different performances, as well as integral artificial teeth and denture base layers. In a preferred embodiment of the invention the denture base and artificial tooth layers are preferably shaped by a molding, spraying, packing, flowing, injecting, pouring or jetting method, which is then bonded to desired block, disk or other forms in partially cured, fully cured or uncured stages. In addition, bonding agent may be applied between layers for some materials. The dental block, disk or other forms are formed from polymeric dental materials, the combinations of polymeric dental materials and polymerizable dental materials, and polymerizable dental materials. The dental block, disk or other forms are formed from polymerizable dental materials, which may include one or more initiating systems to cause them to harden promptly. These materials may solidify once they are dispensed and cooled down on desired locations. These materials can be cured by light or heat once they are applied on desired locations. These materials can also have two parts, which are in situ mixed upon dispensing and polymerized by chemical reactions to form desired shapes.

After the shaping and polymerization of the multiple layered materials, there are the integral connected multiple layered denture base and integral connected artificial teeth that are well bonded to the denture base. The integral connected artificial teeth provide superior tooth retention compared to conventional denture fabrication process. In the dental device, the artificial teeth are integrally connected and bonded to the denture base. Optional, a portion of the tooth material flows through the interface into the adjacent layer of denture base. The adjacent denture base includes various denture base materials. A wide range of denture base and artificial tooth materials may be used here to offer various performances.

A room temperature or heat activating polymerizable denture base or artificial tooth materials preferably include a room temperature (chemical) or heat activating catalyst system. Examples of initiators, include, but are not limited to, dibenzoyl peroxide (BPO), dilauroyl peroxide (LPO), t-butylhydroperoxide, cumene hydroperoxide, di-t-butyl peroxide, dicumyl peroxide, acetyl peroxide, 1-benzyl-5-phenylbarbituric acid (PBS), 5-n-butylbarbituric acid (BBS), an organic peroxide and an amine, an amine and a sulfinic acid salt, an acidic compound and an aryl borate, barbituric acid and alkylborane, barbituric acid and alkyl ammonium chloride/copper chloride, 2,2'-azobis-(isobutyronitrile) (AIBN), 2,2'-azobis-(2,4-dimethyl valeronitrile) (ADMV), tert-butyl per-2-ethyhexanoate (t-BPEH), etc. Other initiating components may include, but are not limited to room temperature or heat activating catalyst components (e.g., system) for curing polymerizable materials (e.g., dental materials) of the invention. For example a peroxide capable of producing free radicals when activated by a reducing agent at room temperature or by heating. Room temperature activated polymerization initiating compounds may preferably include the combinations of peroxide and amine, barbituric acid and copper and chloride ions. Heat-activated polymerization initiating compounds may be included to provide a heat-curable polymerizable material. The peroxides generate free radicals to initiate polymerization and hardening of the composition at elevated temperature. A light activating catalyst system is also preferably included in the polymerizable denture base or artificial tooth materials. A light sensitizer will be included, such as camphorquinone, or methyl benzoin which causes polymerization to be initiated upon exposure to activating wavelengths of light; and/or a reducing compound, for example tertiary amine. Photoinitiators selected from the class of acylphosphine oxides can also be used. These compounds include, for example, monoacyl phosphine oxide derivatives, bisacyl phosphine oxide derivatives, and triacyl phosphine oxide derivatives. For example, 2,4,6-trimethylbenzoyl-diphenyl-phosphine oxide (TPO) can be used as the photopolymerization initiator. Cationic polymerization initiators, diaryliodonium and triaryl sulfonium salts, such as 4-octyloxyphenyl-phenyl iodonium hexafluoroantimonate (OPPI), can also be used, which initiates ring opening polymerization as well as volume expansion from phase change to reduce the polymerization shrinkage. Electron-transfer photosensitizers, such as polynuclear aromatic compounds, their substituted analogues, carbazoles, phenothiazines, curcumin, and titanium-complex free radical initiator can also be added.

The denture base and artificial tooth materials used here including dental composite materials, which may optionally include one or more additives that can include, without limitation, at least one filler (e.g., fibers, glass particles or otherwise), an inhibitor, surfactant, or combinations thereof or others. Suitable fillers such as, polyester fibers, nylon fibers, red acetate fibers, highly crosslinked polymer beads, silanized glass or silica beads, etc. may be used. Stabilizers, include, but are not limited to, hydroquinone (HQ), 2,6-ditert-butyl 4-methyphenol (BHT), monomethyl ether hydroquinone (MEHQ), benzoquinone, chloranil, phenol, butyl hydroxyanaline, tertiary butyl hydroquinone (TBHQ), tocopherol (Vitamin E), and the like. Preferably, butylated hydroxytoluene (BHT) and the methyl ether of hydroquinone hydroquinone (MEHQ) are used as the stabilizers (polymerization inhibitors). Other stabilizers, such UV absorbers, may also be used.

Preferably, these polymerizable dental materials may include from about 0 to about 95 percent by weight filler particles. More preferably, these materials include from about 0 to about 85 percent by weight filler. Nanocomposites and ceramers may be used to make these composites/dental materials for this invention. The fillers preferably include both organic and inorganic particulate fillers to further reduce polymerization shrinkage, improve wear resistance and modify the mechanical and physical properties. Commercially available light curable resins and composites, heat or cold curable acrylics, resins or composites can also be used here.

Shape memory polymers (SMPs) included in this invention are especially interesting for use in denture base material layers around denture teeth and at the tissue side of denture. SMP can be cast and cured into any "memorized" shape, specifically the formation of the tissue side layer of denture base. Shape memory polymer systems allow the tissue side layer of denture base be adjusted repeatedly to accommodate the changes of oral cavity. It is especially beneficial to digital denture approaches, where the fit and precision of tissue side layer of denture base depend on the digital information obtained. The major drawback of current intraoral scanning technology is to catch precise tissue side impression since it involves soft oral tissues. This approach allows current intraoral scanning technology to be used chairside since the use of shape memory polymer at tissue side allows the material at tissue side to be adjustable without the need of precise digital impression. For example, thermo-responsive shape memory polymers can be heated above transition temperature to achieve desired shape and cooled down to form desired shape to adapt to the oral cavity. If desired, materials can revert back to original shapes. This process can be repeated to achieve the optimum result. Shape adjustable thermoplastic and thermoset polymer systems are also interested to this invention for use in denture base material layers around denture teeth and at the tissue side of denture. These polymers can be adjusted at elevated temperature and cooled to form desired shapes without revert back to original shape.

Even though this invention describes the use of polymeric and polymerizable materials to make blocks, polymerizable wax-like materials and their variations (e.g., those claimed in U.S. Pat. Nos. 6,592,369 and 7,175,433, etc.) can be used to make uncured disk (or block) or part of uncured disk (or block). Polymeric materials include many thermoset and thermoplastic materials can be used to make various multiple layered disks (or blocks) for different dental application, such as epoxies, acrylics, polystyrene and polystyrene based copolymers, PEEK, PEKK, Nylons, ABS, SAN, polycarbonates, vinyl acetate (EVA) and copolymers, polyurethanes, polymethylpentene, cellulose acetate based polymers, polyolefins and copolymers, synthetic elastomers, silicones, PET, PBT, PPO, and many other thermoplastic and crosslinked polymers and copolymers, etc.

Example 1

Preparation of Oligomer (TBDMA)

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Example 2

Preparation of Urethane Monomer (UCDPMAA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 22.7 grams of 2-hydroxy-3-phenoxy propyl acrylate, 26.6 grams (0.204 mol) of 2-hydroxyethyl methacrylate, 11.5 grams (0.099 mol) of 2-hydroxyethyl acrylate and 0.10 grams of BHT as an inhibitor were added over a period of 70 minutes while the reaction temperature was maintained between 56° C. and 78° C. After about four hours stirring, the heat was turned off, and monomer was collected from the flask as viscous liquid and stored in a dry atmosphere.

Acrylic Liquids

Acrylic and rubber impact modified acrylic liquids were used to mix with the polymer powders to form pourable liquids or packable doughs to fabricate dental devices. Rubber impact modified liquids contain at least one methacrylate or acrylate monomers and crosslinkers. This liquid mixed with polymer powder produced material with desirable handing properties for pourable or packable applications, which cured to form high impact strength dental material with superior fracture toughness.

Example 3

Impact Modified Liquids

A polymerizable dental material was prepared by mixing at room temperature a liquid mixture of 12 grams of rubber impact modifier M731 (from Kaneka Corporation), 4 grams of monomer cyclohexane dimethanol diacrylate (CD406 from Sartomer Company), and 84 grams of methyl methacrylate (MMA) by using a Silverson L4RT high shear mixer.

Example 4

Impact Modified Liquids

A polymerizable dental material was prepared by mixing at room temperature a liquid mixture of 12 grams of rubber impact modifier M731 (from Kaneka Corporation), 4 grams of monomer cyclohexane dimethanol diacrylate (CD406 from Sartomer Company), and 84 grams of methyl methacrylate (MMA) and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 5A

Impact Modified Liquids

A polymerizable dental material was prepared by mixing at room temperature a liquid mixture of 12 grams of rubber impact modifier M731 (from Kaneka Corporation, from 4 to 14 wt %)), 20 grams of the oligomer TBDMA (we can say urethane di(meth)acrylate in general from 4 to 30 wt %) prepared in Example 1, and 68 grams of methyl methacrylate (MMA, from 60 to 90 wt %) by using a Silverson L4RT high shear mixer.

Example 5B

Impact Modified Liquids

A polymerizable dental material was prepared by mixing at room temperature a liquid mixture of 12 grams of rubber impact modifier M731 (from Kaneka Corporation), 10 grams of the monomer prepared in Example 2, and 78 grams of methyl methacrylate (MMA) by using a Silverson L4RT high shear mixer.

Example 5C

Impact Modified Liquids

A polymerizable dental material was prepared by mixing at room temperature a liquid mixture of 12 grams of rubber impact modifier M731 (from Kaneka Corporation), 6 grams of TBDMA prepared in Example 1, 4 grams of monomer cyclohexane dimethanol diacrylate (CD406 from Sartomer Company), and 78 grams of methyl methacrylate (MMA) by using a Silverson L4RT high shear mixer.

Example 6A

Polymerizable Liquids

A polymerizable dental material was prepared by mixing at room temperature a liquid mixture of 7.49 grams of monomer ethylene glycol dimethacrylate (EGDMA), 0.01 gram of hydroquinone and 92.5 grams of methyl methacrylate (MMA).

Example 6B

Polymerizable Liquids

A polymerizable dental material was prepared by dissolving benzoyl peroxide (0.5 wt %), and 2,2-bis(4-methacryloxyphenyl)propane (BPADMA) (17.3 wt %) in the methyl methacrylate (82.2 wt %) at ambient temperature to form a monomer solution.

Example 6C

Polymerizable Liquids

A polymerizable dental material was prepared by dissolving benzoyl peroxide (0.5 wt %), and 2,2-bis(4-methacryloxyphenyl)propane (BPADMA) (8.5 wt %), and the monomer prepared in Example 2 (11.6 wt %) in the methyl methacrylate (79.4 wt %) at ambient temperature to form a monomer solution.

Example 7

Impact Modified Liquids

A polymerizable dental material was prepared by mixing at room temperature a liquid mixture of 9 grams of rubber impact modifier M570 (from Kaneka Corporation), 4 grams of monomer cyclohexane dimethanol diacrylate (CD406 from Sartomer Company), and 87 grams of methyl methacrylate (MMA) by using a Silverson L4RT high shear mixer.

Example 8

Impact Modified Liquids

A polymerizable dental material was prepared by mixing at room temperature a liquid mixture of 9 grams of rubber impact modifier M501 (from Kaneka Corporation), 4 grams of monomer cyclohexane dimethanol diacrylate (CD406 from Sartomer Company); 87 grams of methyl methacrylate (MMA) by using a Silverson L4RT high shear mixer.

Example 9

Impact Modified Liquids

A polymerizable dental material was prepared by mixing at room temperature a liquid mixture of 9 grams of rubber impact modifier M570 (from Kaneka Corporation), 4 grams of monomer 1,12-dodecanedoil dimethacrylate, and 87 grams of ethyl methacrylate (EMA) by using a Silverson L4RT high shear mixer.

Example 10

Impact Modified Liquids

A polymerizable dental material was prepared by mixing at room temperature a liquid mixture of 12 grams of rubber impact modifier M731 (from Kaneka Corporation), 6 grams of monomer 1,12-dodecanedoil dimethacrylate, and 82 grams of ethyl methacrylate (EMA) by using a Silverson L4RT high shear mixer.

Example 11

Impact Modified Liquids

A polymerizable dental material was prepared by mixing at room temperature a liquid mixture of 12 grams of rubber impact modifier M731 (from Kaneka Corporation), 4 grams of monomer 1,12-dodecanediol dimethacrylate, 84 grams of ethyl methacrylate (EMA) and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 12

Impact Modified Liquids

A polymerizable dental material was prepared by mixing at room temperature a liquid mixture of 12 grams of rubber impact modifier M731 (from Kaneka Corporation), 5 grams of monomer 1,12-dodecanediol dimethacrylate, 20 grams of lauryl methacrylate, 65 grams of ethyl methacrylate (EMA) and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 13

Impact Modified Liquids

A polymerizable dental material was prepared by mixing at room temperature a liquid mixture of 6 grams (4 to 12 wt %) of rubber impact modifier M731 (from Kaneka Corporation), 5 grams of monomer 1,12-dodecanedoil dimethacrylate (0 to 10 wt %), 15 grams of Grindsted Soft-N-Safe (Danisco) (0 to 20 wt %), 15 grams of lauryl methacrylate (5 to 25 wt %), 23 grams of ethyl methacrylate (EMA, 20 to 60 wt %) 36 grams of methyl methacrylate (0 to 40 wt %) and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 14A

Impact Modified Liquids

A polymerizable dental material was prepared by mixing at room temperature a liquid mixture of 9 grams of rubber impact modifier M731 (from Kaneka Corporation), 6 grams of monomer 1,12-dodecanediol dimethacrylate, 10 grams of lauryl methacrylate, 2.5 grams of CN980 (from Sartomer), 70 grams of ethyl methacrylate (EMA), 2.5 grams of MMA and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 14B-1

Impact Modified Liquids

A polymerizable dental material was prepared by mixing at room temperature a liquid mixture of 6 grams of rubber impact modifier M731 (from Kaneka Corporation), 6 grams of monomer 1,12-dodecanediol dimethacrylate, 35 grams of Butyl diglycol methacrylate (BDGMA), 53 grams of MMA and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 14B-2

Impact Modified Liquids for Shape Memory Polymer Layer

A polymerizable dental material was prepared by mixing at room temperature a liquid mixture of 6 grams of rubber impact modifier M731 (from Kaneka Corporation, 4 to 12 wt %), 6 grams of monomer 1,12-dodecanediol dimethacrylate or urethane di(meth)acrylate (4 to 20%), 35 grams of Butyl diglycol methacrylate (BDGMA, 10 to 50 wt %), 53 grams of MMA (20 to 60 wt %). Polymer powder for shape memory polymer layer such as: MMA, EMA and BMA based copolymer [methyl (meth)acrylate, ethyl (meth)acrylate and butyl (meth)acrylate].

Example 15

Impact Modified Liquids

A polymerizable dental material was prepared by mixing at room temperature a liquid mixture of 6 grams of rubber impact modifier C223 (from Arkema), 4 grams of monomer cyclohexane dimethanol diacrylate (CD406 from Sartomer), 10 grams of 2-phenoxyethyl methacrylate, 80 grams of MMA and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Example 16

Polymerizable Liquids

A polymerizable dental material was prepared by mixing at room temperature a liquid mixture of 4 grams of 1,4-butanediol dimethacrylate (BDMA), 0.3 gram of Tinuvin P, and 92.5 grams of methyl methacrylate (MMA) and an initiating package [containing soligen copper, water, succinic acid, hydroquinone, and BAC-Esterchloride (β-phenylethyl-dibutylacetic acid-ethylester-ammonium chloride)].

Example 17

Impact Modified Liquids

A polymerizable dental material was prepared by mixing at room temperature a liquid mixture of 6 grams of rubber impact modifier M731 (from Kaneka Corporation), 5 grams of monomer 1,12-dodecanedoil dimethacrylate, 15 grams of Grindsted Soft-N-Safe (Danisco), 15 grams of lauryl methacrylate, 59 grams of ethyl methacrylate (EMA) and an initiating package [containing soligen copper, water, methacrylic acid, hydroquinone, and BAC-Esterchloride (β-phenylethyl-dibutylacetic acid-ethylester-ammonium chloride)] by using a Silverson L4RT high shear mixer.

Polymer Powders

Polymer powders were used to mix with the impact modified liquid to form pourable liquids or packable doughs to fabricate dental devices. Polymer powders contain at least one selected from methyl methacrylate based polymers, copolymers, crosslinked polymers, plasticized polymers, rubber impact modified polymers or their combinations. These polymer powders mixed with impact modified liquids produced materials with desirable handing properties for pourable or packable applications, which cured to form high impact strength dental materials with superior fracture toughness.

Example 18

Polymer Powders

A polymer powder was prepared by mixing 75% Colacryl TS 1785/1 (from Lucite International) and 25% Colacryl TS 1785/1 (from Lucite International) containing milled pigments and initiators.

Example 19A

Polymer Powders

A polymer powder was prepared by mixing 75% Colacryl TS 1785/1 (from Lucite International) and 25% Colacryl TS 1785/1 (from Lucite International) containing milled pigments.

Example 19B

Polymer Powders

A polymer powder was prepared by mixing 75% rubber impact modified polymer (CTH polymer from Dentsply Caulk) and 25% rubber impact modified CTH polymer containing milled pigments.

Example 19C

Polymer Powders

A polymer powder was prepared by mixing 66.6% lightly crosslinked PMMA polymer (crosslinked with ethylene glycol dimethacrylate), 23.4% PMMA polymer and 10% PMMA polymer containing milled pigments.

Example 19D

Polymer Powders

A polymer powder was prepared by mixing 66.6% lightly crosslinked PMMA polymer (crosslinked with ethylene glycol dimethacrylate), 31.4% PMMA polymer and 2% PMMA polymer containing milled pigments.

Example 20

Polymer Powders

A polymer powder was prepared by mixing 75% Colacryl TS 1785/1 (from Lucite International)), and 25% Colacryl TS 1785/1 containing milled pigments and PBS/BBS based initiators.

Example 21

Polymer Powders

A polymer powder was prepared by mixing 98% Colacryl TS 1388 (from Lucite International) and pigments, and 2% Colacryl TS 1785/1 containing PBS/BBS based initiators.

Example 22

Polymer Powders

A polymer powder was prepared by mixing 70% to 95% (75%-90%) (e.g., 85%) of MMA, EMA and BMA based copolymer, methyl (meth)acrylate, ethyl (meth)acrylate and butyl (meth)acrylate] such as MMA, EMA and BMA based copolymer, methyl (meth)acrylate, ethyl (meth)acrylate and butyl (meth)acrylate] Colacryl TS 1388 (from Lucite International) and 15% Colacryl TS 1388 containing pigments, and PBS/BBS based initiators.

Example 23

Polymer Powders

A polymer powder was prepared by mixing 98% Colacryl TS 2221 (from Lucite International) and pigments, and 2% Colacryl TS 1785/1 containing milled pigments and initiators.

Example 24

Polymer Powders

A polymer powder was prepared by mixing 90% Colacryl TS 2027 (from Lucite International), and 10% Colacryl TS 1785/1 containing milled pigments and initiators.

Example 25

Polymer Powders

A polymer powder was prepared by mixing 85% Colacryl TS 2027 (from Lucite International), and 15% Colacryl TS 2027 containing milled pigments and initiators.

Dental Material Mixtures

Polymerizable dental material mixtures were prepared by mixing polymer powders and rubber impact modified liquids to form pourable liquids or packable doughs for subsequent fabrication of dental devices, such as blocks, disks or other shaped objects. Pourable liquids were used with pouring or injection techniques to fabricate dental devices. Packable doughs were used by packing or injection techniques and heat/cold cured to form dental devices.

Example 26A

Acrylic Dough

The benzoyl peroxide (0.5 wt %), and 2,2-bis(4-methacryloxyphenyl)propane (BPADMA) (17.3 wt %) were dissolved in the methyl methacrylate (82.2 wt %) at ambient temperature to form a monomer solution, then mixed with enamel polymer powders (46:54 weight ratio of liquid to powder) to form a visibly homogeneous dough. A suitable gel-like consistency for molding enamel layer of prosthetic teeth was obtained after aging at ambient temperature.

Example 26B

Acrylic Dough

The benzoyl peroxide (0.5 wt %), and 2,2-bis(4-methacryloxyphenyl)propane (BPADMA) (17.3 wt %) were dissolved in the methyl methacrylate (82.2 wt %) at ambient temperature to form a monomer solution, then mixed with dentin polymer powders (46:54 weight ratio of liquid to powder) to form a visibly homogeneous dough. A suitable gel-like consistency for molding dentin layer of prosthetic teeth was obtained after aging at ambient temperature.

Example 26C

The benzoyl peroxide (0.5 wt %), 2,2-bis(4-methacryloxyphenyl)propane (BPADMA) (16 wt %), the reaction product of example 2 (22.5 wt %) and ethylene glycol dimethacrylate (7 wt %) were dissolved in the methyl methacrylate (54 wt %) at ambient temperature to form a monomer solution, then mixed with polymer powders (48:52 weight ratio of liquid to powder) to form a visibly homogeneous dough. The enamel layers of prosthetic teeth were molded from the resultant precursor blend mixture after it was aged at ambient temperature. A suitable gel-like consistency for molding prosthetic teeth was obtained after aging at ambient temperature.

Example 26D

The benzoyl peroxide (0.5 wt %), 2,2-bis(4-methacryloxyphenyl)propane (BPADMA) (8.5 wt %), and the reaction product of example 2 (11.6 wt %) were dissolved in the methyl methacrylate (79.4 wt %) at ambient temperature to form a monomer solution, then mixed with polymer powders (46:54 weight ratio of liquid to powder) to form a visibly homogeneous dough. The dentin layers of prosthetic teeth were molded from the resultant precursor blend mixture after it was aged at ambient temperature. A suitable gel-like consistency for molding prosthetic teeth was obtained after aging at ambient temperature.

Example 27

Acrylic Dough

A mixture is made from 10 grams of mixture made in Example 5A mixed with 20 grams of polymer powders made in Example 19A to form a visibly homogeneous liquid. A suitable gel-like consistency for molding denture base was obtained after aging at ambient temperature for 10 minutes.

Example 28A

Light Curable Material

A polymerizable dental material was prepared by stirring at ambient temperature a liquid mixture of 320 grams of oligomer (20 to 40 wt %) made following the procedure of Example 1, 300 grams of ethoxylated$_{10}$ bisphenol A dimethacrylate (SR480 from Sartomer, 20 to 40 wt %), 300 grams of 2-phenoxyethyl methacrylate (SR340 from Sartomer, 20 to 40 wt %); 60 grams of rubber impact modifier M731 (from Kaneka Corporation, 4 to 12 wt %), 19 grams of initiator [2,4,6-trimethylbenzoyldiphenylphosphine oxide, (Lucirin TPO available from BASF, 0.1 to 2%)].

Example 28B

Light Curable Material

A polymerizable dental material was prepared by stirring at ambient temperature a liquid mixture of 32 grams of oligomer made following the procedure of Example 1, 50 grams of methyl methacrylate (MMA), 10 grams of 2-phenoxyethyl acrylate (SR339 from Sartomer), 6 grams of rubber impact modifier S2006 (from Mitsubishi Rayon Co.), 1.0 gram of 2,4,6-trimethylbenzoyldiphenylphosphine oxide, (Lucirin TPO available from BASF); and 1 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 29

Light Curable Material

A polymerizable dental material was prepared by stirring at ambient temperature a liquid mixture of 32 grams of oligomer made following the procedure of Example 1, 30 grams of ethoxylated$_{10}$ bisphenol A dimethacrylate (SR480 from Sartomer), 30 grams of tetrahydrofurfury methacrylate (SR203 from Sartomer); 6 grams of rubber impact modifier M731 (from Kaneka Corporation), 1.9 grams of 2,4,6-trimethylbenzoyldiphenylphosphine oxide, (Lucirin TPO available from BASF), and 0.1 gram of butylated hydroxytoluene (BHT).

Example 30

Light Curable Material

A polymerizable dental material was prepared by stirring at ambient temperature a liquid mixture of 10 grams of oligomer (TBDMA, 5 to 15 wt %) made following the procedure of Example 1, 10 grams of lauryl methacrylate (SR213 from Sartomer, 0 to 20 wt %), 10 grams of 2-phenoxyethyl methacrylate (SR340 from Sartomer, 0 to 20 wt %), 50 grams of tetrahydrofurfury methacrylate (SR203 from Sartomer, 0 to 60 wt %), 10 grams of polycaprolactones (CPAP2125 from Perstorp UK limited, 0 to 15 wt %), 9 grams of rubber impact modifier M731 (from Kaneka Corporation), and 1 gram of initiator [2,4,6-trimethylbenzoyldiphenylphosphine oxide, (Lucirin TPO available from BASF, 0.1 to 2%)].

Example 31

Light Curable Material

A polymerizable and semi-crystallizable dental material was prepared by stirring at ambient temperature a liquid mixture of 10 grams of lauryl methacrylate (SR213 from Sartomer), 30 grams of 2-phenoxyethyl methacrylate (SR340 from Sartomer), 40 grams of tetrahydrofurfury methacrylate (SR203 from Sartomer), 20 grams of polycaprolactones (CPAP2125 from Perstorp UK limited), 8 grams of rubber impact modifier M731 (from Kaneka Corporation), and 2 gram of 2,4,6-trimethylbenzoyldiphenylphosphine oxide, (Lucirin TPO available from BASF).

Example 32

Pourable Acrylic Disk

A pour acrylic mixture was prepared by mixing 80 grams of polymer powders of Example 18 and 56 grams of liquid of Example 15. This mixture was poured into a previously prepared disk shaped mold and then cured in 55° C. pressure pot for 30 minutes. After cure, a disk form is obtained. Then a second acrylic mixture was prepared by mixing 60 grams of polymer powders of Example 21 and 50 grams of liquid of Example 10. This mixture was quickly and immediately poured into a previously prepared disk shaped mold and then cured in 55° C. pressure pot for 30 minutes. After removal from the mold, a disk form is obtained with a hard layer and a relatively soft layer, which can be used to mill a two layered denture base. The second cured layer can be easily remolded, such as on a stone cast once milled denture is heated to elevated temperature in an oven or a hot water bath.

Example 33

Pourable Acrylic Disk

A pour acrylic mixture was prepared by mixing 70 grams of polymer powders of Example 18 and 50 grams of liquid of Example 15. This mixture was poured into a previously prepared disk shaped mold and then cured in 55° C. pressure pot for 30 minutes. After cure, a disk form is obtained. Then a second acrylic mixture was prepared by mixing 50 grams of polymer powders of Example 21 and 42 grams of liquid of Example 14A. This mixture was quickly and immediately poured into a previously prepared disk shaped mold and then cured in 55° C. pressure pot for 30 minutes. After removal from the mold, a disk form is obtained with a soft layer and a hard layer, which can be used to mill a two layered denture base. The second cured layer can be easily remolded, such as on a stone cast once milled denture is heated to elevated temperature in an oven or in a hot water bath.

Example 34

Pourable Acrylic Disk

A pour acrylic mixture was prepared by mixing 80 grams of polymer powders of Example 18 and 56 grams of liquid of Example 15. This mixture was poured into a previously prepared disk shaped mold and then cured in 55° C. pressure pot for 30 minutes. After cure, a disk form is obtained. Then a second acrylic mixture was prepared by mixing 60 grams of polymer powders of Example 22 and 50 grams of liquid of Example 13. This mixture was quickly and immediately poured into a previously prepared disk shaped mold and then cured in 55° C. pressure pot for 30 minutes. After removal from the mold, a disk form is obtained with a very soft layer and a hard layer, which can be used to mill a two layered denture base. The second cured layer can be easily remolded, such as on a stone cast once milled denture is heated to elevated temperature in an oven or in a hot water bath. It may also be adjusted at chairside, which can be heated and then adjusted in patient's mouth to get the improved fit and adaptation. Repeat adjustment is possible if desired.

Example 35

Packable Acrylic Disk

A packable acrylic mixture was prepared by mixing 90 grams of polymer powders of Example 18 and 45 grams of liquid of Example 3. This mixture was packed into a previously prepared disk shaped mold and then cured in 63° C. water tank for 90 minutes and boil out tank for 30 minutes. After cure, a disk form is obtained. Then a second acrylic mixture was prepared by mixing 60 grams of polymer powders of Example 25 and 50 grams of liquid of Example 10. This mixture dough was packed onto a previously cured disk shaped form in a mold and then cured in 63° C. water tank for 90 minutes and boil out tank for 30 minutes. After removal from the mold, a disk form is obtained with a soft layer and a hard layer, which can be used to mill a two layered denture base. The second cured layer can be easily remolded, such as on a stone cast once milled denture is heated to elevated temperature in an oven or a hot water bath.

Example 36

Packable Acrylic Disk

A packable acrylic mixture was prepared by mixing 90 grams of polymer powders of Example 19B and 45 grams of liquid of Example 6A. This mixture was packed into a previously prepared disk shaped mold and then cured in 63° C. water tank for 90 minutes and boil out tank for 30 minutes. After cure, a disk form is obtained. Then a second acrylic mixture was prepared by mixing 60 grams of polymer powders of Example 24 and 40 grams of liquid of Example 9. This mixture dough was packed onto a previously cured disk shaped form in a mold and then cured in 63° C. water tank for 90 minutes and boil out tank for 30 minutes. After removal from the mold, a disk form is obtained with a relatively soft layer and a hard layer, which can be used to mill a two layered denture base. The second cured layer can be easily remolded, such as on a stone cast once milled denture is heated to elevated temperature in an oven or a hot water bath.

Example 37

Packable Acrylic Disk

A packable acrylic mixture was prepared by mixing 60 grams of polymer powders of Example 21 and 40 grams of liquid of Example 14A. This mixture dough was packed onto a previously prepared disk shaped mold and then cured in 63° C. water tank for 90 minutes and boil out tank for 30 minutes. A cured disk form is formed in the bottom of the mold. Then a second acrylic mixture was prepared by mixing 80 grams of polymer powders of Example 18 and 40 grams of liquid of Example 3. This mixture was packed onto above prepared disk in the mold and then cured in 63° C. water tank for 90 minutes and boil out tank for 30 minutes. A two layered disk form is obtained in the mold. Finally, about 80 grams of tooth acrylic dough prepared from Example 26B was packed on top of the cured disk shaped form in a mold and then cured under 10,000 psi pressure for 90 minutes with heat (up to 120° C.) from bottom up through cured disk. After removal from the mold, a disk form is obtained with a tooth layer, a soft denture base layer, and a hard denture base layer, which can be used to mill a denture and paint or apply sealer to achieve desired results. The first cured layer can be easily remolded, such as on a stone cast once milled denture is heated to elevated temperature in an oven or a hot water bath.

Example 38

Packable Acrylic Disk

A packable acrylic mixture was prepared by mixing 60 grams of polymer powders of Example 21 and 40 grams of liquid of Example 14A. This mixture dough was packed onto a previously prepared disk shaped mold and then cured in 63° C. water tank for 90 minutes and boil out tank for 30 minutes. A cured disk form is formed in the bottom of the mold. Then a second acrylic mixture was prepared by mixing 80 grams of polymer powders of Example 18 and 40 grams of liquid of Example 3. This mixture was packed onto above cured disk in the mold and then cured in 63° C. water tank for 90 minutes and boil out tank for 30 minutes. A two layered disk form is obtained in the mold. Then, a about 60 grams of tooth dentin shaded third acrylic dough prepared according to Example 26B was packed on top of the cured disk shaped form in a mold and then cured under 10000 psi pressure for 90 minutes with heat (bottom plate set at 200 F) from bottom up through cured disk to form a dentin layer. Finally, about 30 grams of tooth enamel shaded acrylic dough prepared according to Example 26A was packed on top of the cured disk shaped form in a mold and then cured under 10000 psi pressure for 120 minutes with heat (bottom plate set at 200 F) from bottom up through cured disk to form an enamel layer. After removal from the mold, a disk form is obtained with a tooth enamel layer, tooth dentin layer, a soft denture base layer, and a hard denture base layer, which can be used to mill a denture and paint or apply sealer to achieve desired results. The first cured layer can be easily remolded, such as on a stone cast once milled denture is heated to elevated temperature in an oven or a hot water bath.

Example 39

Packable Acrylic

About 30 grams of tooth enamel shaded tooth acrylic dough prepared according to Example 26A was packed on top of the cured disk shaped form in a mold and then cured under 10000 psi pressure for 120 minutes with heat (bottom plate set at 200 F) from bottom up to form an enamel disk layer. Then, about 90 grams of tooth dentin shaded acrylic dough prepared according to Example 26 was packed on top of the cured disk shaped form in a mold and then cured under 10000 psi pressure for 120 minutes with heat (bottom plate set at 200 F) from bottom up through cured enamel disk layer to form a dentin disk layer. A packable acrylic mixture was prepared by mixing 80 grams of polymer powders of Example 18 and 60 grams of liquid of Example 15. This denture base liquid mixture was poured on top of the cured disk shaped enamel and dentin layers in the mold and then cured in 45° C. pressure pot for 30 minutes. Then second denture base dough was prepared by mixing 30 grams of polymer powders of Example 25 and 25 grams of liquid of Example 14B. This denture base liquid mixture was poured onto above cured disk shaped form and then cured in 45° C. pressure pot for 30 minutes. A multiple layered disk form is obtained in the mold. After removal from the mold, a disk form is obtained with a tooth enamel layer, tooth dentin layer, a soft denture base layer, and a hard denture base layer, which can be used to mill a denture and paint or apply sealer to achieve desired results.

Example 40

Light and Self-Cure Disk

A light curable material was prepared according to Example 30. About 80 grams of this material was poured into a previously prepared disk shaped mold and then cured in Eclipse light unit (sold by Dentsply Sirona) for 10 minutes and flip cured for another 10 minutes. After cure, a disk form is obtained. Then a second light curable material was prepared according to Example 28. About 40 grams of this second light curable material was poured on top of the previously prepared disk in disc shaped mold and then cured for 10 minutes in Eclipse light unit. Then additional 40 grams of this second light curable material was added on top the cured layer and then cured for 10 minutes in Eclipse light unit. Finally, another 40 grams of this second light curable material was added on top the cured layer and then cured for 10 minutes in Eclipse light unit to form the final disk form. After removal from the mold, a disk form is obtained with a soft layer and a hard layer, which can be used to mill a two layered denture base. The second cured layer can be easily remolded, such as on a stone cast once milled denture is heated to elevated temperature in an oven or a hot water bath. It may also be adjusted at chairside, which can be heated and then adjusted in patient's mouth to get the improved fit and adaptation. Repeat adjustment is possible if desired.

Example 41

A Light Curable Disk

A light curable material was prepared according to Example 30. About 80 grams of this material was poured into a previously prepared disk shaped mold and then cured in Eclipse light unit (sold by DENTSPLY Sirona) for 10 minutes and flip cured for another 10 minutes. After cure, a disk form is obtained. Then a second light curable material was prepared according to Example 28. About 40 grams of this second light curable material was poured on top of the previously prepared disk in disc shaped mold and then cured for 10 minutes in Eclipse light unit. Then additional 40 grams of this second light curable material was added on top the cured layer and then cured for 10 minutes in Eclipse light unit. Finally, another 40 grams of this second light curable material was added on top the cured layer and then cured for 10 minutes in Eclipse light unit to form the final disk form. After removal from the mold, a disk form is obtained with a soft layer and a hard layer, which can be used to mill a two layered denture base. The second cured layer can be easily remolded, such as on a stone cast once milled denture is heated to elevated temperature in an oven or a hot water bath. It may also be adjusted at chairside, which can be heated and then adjusted in patient's mouth to get the improved fit and adaptation. Repeat adjustment is possible if desired.

Wear Resistance Tests

Wear resistance was tested using a three-body cyclic abrasion wear machine (Leinfelder method) at 37° C. Localized wear was measured by determining volume loss in $mm^3$ after 400,000 cycles at 50 RPM. The wear data as volume loss are listed in Table 1.

TABLE 1

Wear loss of tooth materials tested at 37° C.

| Material | Volume loss (37° C., mm³) | S.D. |
|---|---|---|
| Example 26A | 0.045-0.105 (0.060-0.090) 0.075 | 0.015 |
| Example 26C | 0.040-0.080 (0.050-0.070) 0.059 | 0.010 |
| Example 26D | 0.045-0.105 (0.060-0.090) 0.074 | 0.015 |
| Example 26E | 0.060-0.120 (0.075-0.110) 0.093 | 0.017 |

Flexural Property Tests

Flexural Strength and Flexural Modulus of the polymerized compositions of denture tooth materials were measured with crosshead speed of 1 mm/minute by using three-point bend test on Instron bending unit according to ISO. Samples (2 mm×2 mm×25 mm) from Examples 1 to 6 were molded in metal molds with the same curing cycles and post cure in 260° F. oven for two hours. The flexural strength and flexural modulus of tooth materials are shown in Table 2.

TABLE 2

Flexural strength and flexural modulus of tooth materials tested at ambient temperature.

| Material | Flexural Strength (MPa) | Modulus (MPa) |
|---|---|---|
| Example 26A | 115-145 (120-140) 131 (sd = 5) | 2450-3200 (2650-3000) 2875 (sd = 185) |
| Example 26C | 120-170 (130-160) 140 (sd = 7) | 2800-3650 (3000-3450) 3268 (sd = 162) |
| Example 26D | 125-145 (130-140) 134 (sd = 3) | 2700-3300 (2850-3150) 2944 (sd = 121) |
| Example 26E | 120-140 (125-135) 129 (sd = 2) | 2750-3050 (2800-2950) 2893 (sd = 57) |

For denture base materials, flexural Strength and Flexural Modulus of the polymerized acrylic compositions were measured by using three-point bend test on Instron bending unit according to ASTM 790 (1997). Samples were prepared according to ISO 20795-1:2008 (E) and cured in flasks containing silicone and stone molds in pressure pot or in a water tank or cured in a EPU light unit (sold by Dentsply International) for 10 minutes. The flexural data for denture base samples prepared are illustrated in Table 3.

TABLE 3

Flexural strength and flexural modulus of denture base materials of this invention tested at 37° C.

| Material | Flexural Strength (MPa) | Modulus (MPa) |
|---|---|---|
| Example 27* | 76.5-80 (77.5-79.5) 78.4 (sd = 0.5) | 2300-2550 (2350-2500) 2420 (sd = 30) |
| Example 28A | 72.0-77.0 (73.0-76.0) 74.5 (sd = 0.9) | 2400-2700 (2500-2600) 2550 (sd = 35) |
| Example 28B | 95-105 (97-103) 99.3 (sd = 2.1) | 3000-3400 (3100-3300) 3190 (sd = 62) |
| Example 29 | 74.0-79.0 (75.0-78.0) 76.2 (sd = 0.8) | 2300-2750 (2400-2650) 2520 (sd = 30) |

*The flexural specimens (3.3 mm × 10 mm × 64 mm) were stored in 37° C. water for 50 hours, immediately laid on the supports of the flexural test rig immersed in the 37° C. water bath and allowed the specimen to come to equilibrium with the water bath temperature. Then the flexural properties were determined using three point flexure test with a span of 50 mm at an Instron crosshead speed of 5 mm/minute and loaded to break according to ISO20795-1: 2013.

Fracture Toughness Tests

Fracture toughness of the polymerized compositions of denture tooth materials was measured by Instron with a crosshead speed of 0.6 mm/minute. Cylindrical short rod fracture toughness test specimens were machined and tested in accordance with ASTM E1304-97 [Standard Test Method for Plane-Strain (Chevron Notch) Fracture Toughness of Metallic Materials]. Chevron-cut samples were placed into 37° C. deionized water for 24 hours, followed by 1 hour at 23° C. deionized water prior to testing. The flexural toughness of various tooth materials is shown in Table 4.

TABLE 4

Fracture toughness of tooth materials tested at ambient temperature.

| Material | $K_{max}$ (MPa m$^{1/2}$) |
|---|---|
| Example 26A | 1.5-2.3 (1.7-2.15) 1.91 (sd = 0.15) |
| Example 26C | 1.3-2.0 (1.5-1.9) 1.72 (sd = 0.14) |
| Example 26D | 1.5-2.5 (1.75-2.25) 1.99 (sd = 0.18) |
| Example 26E | 1.9-2.7 (2.1-2-5) 2.32 (sd = 0.13) |

Fracture toughness specimens for denture base materials were prepared, notched to a depth of 3 mm and stored in 37° C. water for 7 days and tested with a span of 32 mm at a crosshead speed of 1 mm/minute until maximum load was passed and the crack had almost reached the opposite side of the specimen according to ISO20795-1:2013. The toughness data are listed in Table 5.

TABLE 5

Fracture toughness of materials of this invention tested at ambient temperature.

| Material | $K_{max}$ (MPa m$^{1/2}$) | Work (J/m$^2$) |
|---|---|---|
| Example 27 | 2.75-3.25 (2.85-3.1) 2.96 (sd = 0.12) | 1900-2200 (1950-2125) 2040 (sd = 80) |
| Example 28A | 2.0-2.4 (2.1-2.3) 2.22 (sd = 0.03) | 3500-5500 (4000-5000) 4470 (sd = 410) |
| Example 28B | 2.6-3.0 (2.7-2.9) 2.82 (sd = 0.09) | 1250-2050 (1450-1850) 1640 (sd = 180) |
| Example 29 | 1.9-2.3 (2.0-2.2) 2.08 (sd = 0.09) | 4000-6900 (4800-6200) 5460 (sd = 680) |

It should be understand that while the present invention has been described with respect to certain specific embodiments thereof, it should not be considered limited to such embodiments but may be used in other ways without departure from the spirit of the invention and the scope of the appended claims. The present invention describes mainly denture and denture base, it should be understand that can be referred to splint, nightguard, retainer, aligner, flipper, flexible partial, and many other dental devices.

The invention claimed is:

1. A method for making a multilayered block or disk comprising the steps of:
   providing a mold;
   placing a first polymerizable material in the mold to form a first layer, the first polymerizable material including a mixture of:
      a powder blend of 65% to 85% by wt a [methyl (meth)acrylate, ethyl (meth)acrylate and butyl (meth)acrylate] copolymer; and a first initiator; and
      a liquid blend of 4-15% by wt a first rubber impact modifier; at least one monomer; and
      a second initiator;
   placing a second polymerizable material in contact with the first layer of the polymerizable material to form a second polymerizable layer, wherein the second polymerizable material is different than the first polymerizable material and includes a mixture of:
- a powder blend having of 75% to about 95% by wt [methyl (meth)acrylate, ethyl (meth)acrylate and butyl (meth)acrylate] copolymer; and a third initiator;
- a liquid blend of 4-12% by wt a second rubber impact modifier being different than the first rubber impact modifier; 1-10% by wt of at least one dimethacrylate component; and 20-70% by wt at least one methacrylate based component, and a fourth initiator;

curing the first polymerizable material to form a cured first polymerizable material;

curing the second polymerizable material to form a second polymerizable material, the cured first polymerizable material and the cured second polymerizable material form the multilayered block or disk;

wherein the cured second polymerizable material has a higher Tg than the cured first polymerizable material.

2. The method of claim 1, wherein the cured first polymerizable material has flexural strength ranging from 70 to 110 MPa.

3. The method of claim 1, wherein the cured first polymerizable material has a flexural modulus ranging from 2000 to 3500 MPa.

4. The method of claim 1, wherein the cured second polymerizable material has flexural strength ranging from 115 MPa to 200 MPa.

5. The method of claim 1, wherein the cured second polymerizable material has a flexural modulus ranging from 2400 MPa to 3700 MPa.

6. The method of claim 1, wherein the first polymerizable material is cured prior to the curing of the second polymerizable material.

7. The method of claim 1, wherein the step of placing the second polymerizable material occurs after the step of curing the first polymerizable material.

8. The method of claim 1, wherein the first layer of polymerizable material, after being cured includes recesses for receiving the second polymerizable material.

9. The method of claim 8, wherein the cured first layer of polymerizable material forms a denture base and the cured second layer of polymerizable material forms a plurality of teeth after a further step of milling or grinding the multilayered block or disk.

10. The method of claim 8, wherein the second polymerizable material extends above the recesses while forming the second layer of polymerizable material.

11. The method of claim 1, wherein the step of curing the first polymerizable material and the step of curing the second polymerizable material occur at the same time.

12. The method of claim 1, further comprising the step of placing a third polymerizable material in contact with the second layer of polymerizable material to form a third layer of polymerizable material.

13. The method of claim 12, wherein the step of placing the third polymerizable material occurs after the step of curing the second layer of polymerizable material.

14. The method of claim 13, further comprising the step of curing the third layer of polymerizable material.

15. The method of claim 1, wherein the cured first layer of polymerizable material around recesses formed therein having the cured second polymerizable material, after being milled or grinded is adjustable while the remaining areas of the cured first polymerizable material and the cured second polymerizable material remain shape stable at elevated temperatures up to 100° C.

16. The method of claim 1, wherein the curing steps, the first polymerizable material and the second polymerizable material are partially cured to form a partially cured multilayered disk or block.

17. The method of claim 1, further comprising the steps of:
- milling or grinding the partially cured multilayered block or disk to form a partially cured dental component; and
- curing the milled or ground partially cured block or disk to form a fully cured dental component.

18. The method of claim 17, wherein the fully cured dental component is a denture having a denture base formed for the milled or ground fully cured first polymerizable material and a plurality of teeth formed from the milled or ground fully cured second polymerizable material.

19. The method of claim 18, wherein the top surface of the teeth formed from the milled or ground fully cured second polymerizable material has a high wear resistance determined by volume loss ranging from 0.045-0.120 mm3 at 37° C. (after 400,000 cycles at 50 RPM).

* * * * *